United States Patent [19]

Dabill et al.

[11] Patent Number: 4,457,954
[45] Date of Patent: Jul. 3, 1984

[54] CATALYTIC GAS-SENSITIVE ELEMENTS

[75] Inventors: David W. Dabill; Stephen J. Gentry, both of Deepcar; Nicholas W. Hurst; Alan Jones, both of Sheffield; Peter T. Walsh; Thorpe Hesley, all of England

[73] Assignee: National Research Development Corporation, London, England

[21] Appl. No.: 297,502

[22] Filed: Aug. 28, 1981

[30] Foreign Application Priority Data

Sep. 5, 1980 [GB] United Kingdom ............... 8028675
Aug. 6, 1981 [GB] United Kingdom ............... 8124036

[51] Int. Cl.$^3$ ............................................ G01N 27/16
[52] U.S. Cl. ................................. 427/125; 422/97; 422/98; 427/126.4
[58] Field of Search ............................. 422/94–98, 422/90; 338/225 D, 34; 427/125, 49, 126.4

[56] References Cited

U.S. PATENT DOCUMENTS

| 3,883,307 | 5/1975 | Kim ..................................... 422/97 |
| 4,072,467 | 2/1978 | Jones . |
| 4,111,658 | 9/1978 | Firth et al. . |
| 4,193,964 | 3/1980 | John . |
| 4,303,612 | 12/1982 | Sonley ................................. 422/97 |
| 4,416,911 | 11/1983 | Wilkinson-Tough ................. 427/12 |

FOREIGN PATENT DOCUMENTS

| 004184 | 9/1979 | European Pat. Off. . |
| 2942722 | 5/1980 | Fed. Rep. of Germany . |
| 1321520 | 6/1973 | United Kingdom . |
| 1387412 | 3/1975 | United Kingdom . |
| 1422451 | 1/1976 | United Kingdom . |
| 1501888 | 2/1978 | United Kingdom . |
| 1512708 | 6/1978 | United Kingdom . |
| 1516039 | 6/1978 | United Kingdom . |
| 1549640 | 8/1979 | United Kingdom . |
| 1556339 | 11/1979 | United Kingdom . |
| 2034893 | 6/1980 | United Kingdom . |
| 2066963 | 7/1981 | United Kingdom . |

Primary Examiner—Michael S. Marcus
Attorney, Agent, or Firm—Cushman, Darby & Cushman

[57] ABSTRACT

An element for detecting combustible gases comprises a catalyst material associated with an electrical resistor serving as both a heater and a thermal sensor, the catalyst material being produced by heating a deposit from an aqueous slurry of alumina, of maximum particle size 0.1 micron, containing in solution a compound of a metal of the platinum group. The deposited material may constitute a pellet (6) within which is embedded a coiled part (3) of a wire (1) constituting the resistor. The element then resembles a conventional "pellistor" in form, but has improved resistance to poisoning or inhibition of the catalyst.

20 Claims, 4 Drawing Figures

CATALYTIC GAS-SENSITIVE ELEMENTS

This invention relates to gas-sensitive elements suitable for use in instruments for the detection of combustible gases in oxygen-containing atmospheres, and is concerned in particular with such elements of the kind comprising a catalyst material exposed for contact with a sample of an atmosphere to be tested and associated with an electrical resistor adapted to serve both as a heater for bringing the catalyst material to a temperature at which it can cause combustion of at least one gas to be detected and as a thermal sensor for detecting any thermal effect on the catalyst material caused by the occurrence thereon of a combustion reaction. One conventional form of element of this kind is known as a "pellistor" and is described for example in British Patent Specification No. 892,530. In this form of element the catalyst material is constituted by a surface coating or impregnation of a pellet of refractory material within which is embedded a coiled part of a wire which constitutes the resistor; the pellet has conventionally consisted of alumina formed by decomposition of an aluminium compound such as aluminium nitrate.

A problem that arises in the use of gas-sensitive elements of the kind specified is that the catalyst material is susceptible to poisoning or inhibition (i.e. permanent or temporary impairment of its capacity to cause combustion of the gas to be detected) by certain components commonly present in some kinds of atmosphere that it may be desired to test; examples of such components are silicone vapours, alkyl lead compounds and sulphur compounds. For some applications the problem can be dealt with by causing the gas sample to pass through a suitable material such as active charcoal before it reaches the gas-sensitive element, but this is not always convenient and it would in any event be desirable to provide gas-sensitive elements of the kind specified having a greater intrinsic resistance to poisoning or inhibition than a conventional pellistor.

In European Patent Application Publication No. 0004184 there is disclosed a gas-sensitive element of the kind specified which to some extent meets this objective, at least in respect of poisoning by silicone vapours. The element is in the form of a pellistor having an alumina pellet, the outer part of the pellet being formed by deposition from an aqueous slurry of alumina; the catalyst material is introduced in a similar manner to that described in British Patent Specification No. 892,530, i.e. by applying to the surface of the pellet a solution or dispersion of a compound or compounds of one or more metals of the platinum group. This arrangement has certain disadvantages, arising primarily from the fact that a mass of alumina formed by deposition from an aqueous slurry has relatively low inherent mechanical strength. It is therefore impracticable for the whole pellet to be formed in this way; instead the central part is formed in conventional manner by decomposition of an aluminium compound. This, coupled with the manner of introduction of the catalyst metal has the result that the catalyst metal is virtually limited to the outer part of the pellet. For a pellet of given size, therefore, the total amount of catalyst metal present (which appears to be an important factor in relation to long-term resistance to poisoning and inhibition) will be substantially less than would be the case if the catalyst metal were uniformly distributed through the whole volume of the pellet.

The present invention avoids these disadvantages in providing a gas-sensitive element of the kind specified having a greater intrinsic resistance to poisoning or inhibition than a conventional pellistor.

According to the invention, in a gas-sensitive element of the kind specified the catalyst material is in the form of a coherent mass produced by heating a deposit made from an aqueous slurry of alumina containing in solution at least one compound of a metal of the platinum group, the particle size of the alumina in the slurry being no greater than 0.1 micron.

It should be noted that the maximum particle size quoted is that of individual particles of alumina, and not that of the sponge-like aggregates which tend to form by clustering of the individual particles. By the platinum group is meant the group consisting of platinum, palladium, rhodium, ruthenium, iridium and osmium.

In preferred embodiments of the invention, the coherent mass is in the form of a pellet within which is embedded a coiled part of a wire which constitutes the resistor of the gas-sensitive element. The presence of the catalyst metal in solution in the slurry from which the pellet is formed results in the pellet having a relatively high mechanical strength, and the catalyst metal is of course uniformly distributed through the whole volume of the pellet.

Various arrangements in accordance with the invention will now be described by way of example with reference to the accompanying drawings, in which.

Figure 1:
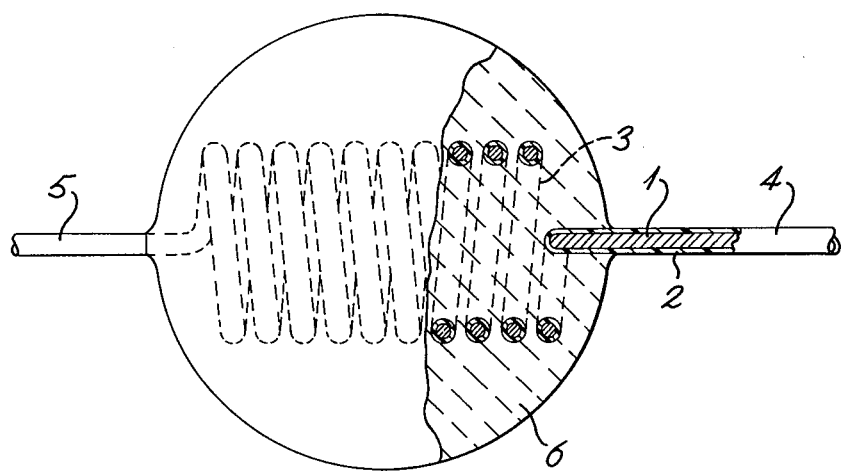
FIG. 1 is a part sectional view of a gas-sensitive element.

The element illustrated in FIG. 1, which is suitable for use in the detection of methane in air, comprises a length of platinum wire 1 of diameter 50 microns, which has formed on it a coating 2 of alumina 15–20 microns thick; the central portion of the coated wire is in the form of a coil 3 consisting of 10–11 turns of pitch about 125 microns and external diameter about 0.7 mm, the ends 4 and 5 of the wire extending away from the coil 3 to provide a means of connecting the coil 3 in an electrical circuit. The coil 3 is embedded in an approximately spherical pellet 6, of diameter in the range 1.5–1.7 mm, which is of subtantially uniform composition. Three examples of different ways of forming the pellet 6 are set out below.

EXAMPLE I

In this case the element is designed to be directly interchangeable with a known type of pellistor having an approximately spherical alumina pellet of diameter about 1.2 mm formed in the conventional manner and utilising a mixture of palladium and thoria as the catalyst material. For fabricating the pellet 6 there is initially prepared an aqueous solution of ammonium chloropalladite —$(NH_4)_2PdCl_4$— and thorium nitrate —$Th(NO_3)_4$— at respective concentrations of 0.45 and 1.18 moles per liter, the pH of the solution being adjusted to a value between 0 and 1 by the incorporation of nitric acid. A slurry is then produced by mixing this solution with gamma alumina having a nominal particle size of 0.05 micron (supplied by B.D.H. Chemicals Ltd), in the proportions of 0.36 gram of alumina to one ml of the solution; the alumina is predominantly in the form of sponge-like aggregates having dimensions in the range 1-5 microns and has a specific surface area in the range 100-120 meters$^2$/gram. Immediately before the formation of the pellet 6 the surface of the alumina coating 2 is prepared by passing a current of 400 mA through the wire 1 for 5-10 seconds. In forming the pellet 6, firstly a small drop of the slurry is applied to the coil 3 from a glass rod or dropper, the amount applied being just sufficient to fill the space within the coil 3, secondly the coil 3 is heated by passing a current of 300 mA through the wire 1 for 5-10 seconds, thirdly a second drop of the slurry is applied to the product of the second step, and fourthly the coil 3 is again heated in the same manner as for the second step. Normally the performance of these four steps will be sufficient to produce an element of the required size, but it may occasionally be necessary, in order to achieve a diameter in the range quoted above for the pellet 6, to apply a third drop of the slurry to the resultant product, with the coil 3 subsequently being heated in the same manner as before. In either event a final heating stage is carried out in which a current of 300 mA is passed through the wire 1 for about 30 seconds. The heating carried out at the various stages drives off the water from the slurry, consolidates the alumina deposit, and decomposes the metal salts to the corresponding oxides; after the final heating stage referred to above, therefore, the pellet 6 consists of a coherent mass of fine-grained alumina bound together by a substantially uniform dispersion of palladium oxide and thoria. In order to enhance and stabilise the sensitivity of the catalyst material constituted by the pellet 6, the element is subjected to a conditioning process which consists of passing a current of 320 mA through the wire 1 while the pellet 6 is exposed for five minutes to air containing 12% methane and then for two minutes to normal air. It appears that during the conditioning process there occurs at least a partial reduction of the palladium oxide to palladium metal.

EXAMPLE II

In this case the initial solution of ammonium chloropalladite and thorium nitrate used in Example I is replaced by an aqueous solution of ammonium chlororhodite —$(NH_4)_2[RhCl_5(H_2O)]$— at a concentration of 0.23 moles per liter. Apart from this the formation of the pellet 6 is carried out in the same manner as for Example I, involving production of the slurry preparation of the surface of the coil 2, application of the slurry and heating, and a final conditioning process, all the numerical details being as quoted for Example I. The pellet 6 then contains rhodium distributed substantially uniformly throughout its volume.

EXAMPLE III

In this case the initial solution of ammonium chloropalladite and thorium nitrate used in Example I is replaced by an aqueous solution of chloroplatinic acid —$H_2PtCl_6$— at a concentration of 0.45 moles per liter. Once again, the procedure used in forming the pellet 6 is otherwise the same as for Example I. The pellet 6 then contains platinum distributed substantially uniformly throughout its volume.

Figure 2:
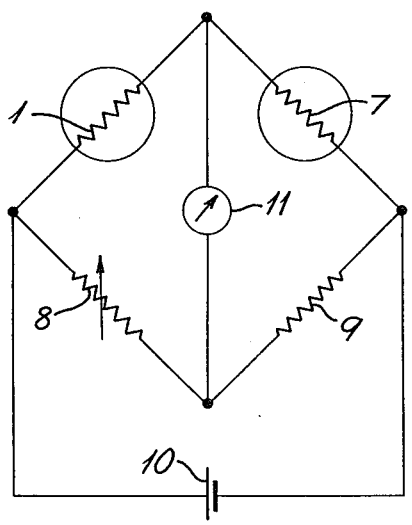
FIG. 2 is a diagram of an electrical circuit in which that element may be used.

In an instrument for detecting methane in air, a gas-sensitive element as described with reference to FIG. 1 may suitably be connected in a conventional Wheatstone bridge circuit, such as is illustrated in basic form in FIG. 2. The four arms of the bridge are respectively constituted by the wire 1 of the element, a resistor 7 forming part of a compensating element and having a resistance approximately equal to that of the wire 1, a variable resistor 8, and a fixed resistor 9 having a value such that the bridge can be balanced by adjustment of the resistor 8; across the two diagonals of the bridge are respectively connected a voltage source 10 and a voltmeter 11. The voltage of the source 10 is chosen (at a value of about 2.5 volts) so that the current passing through the wire 1 when the bridge is balanced will be such as to heat the gas-sensitive element to a temperature in the range 500°-550° C.; at this temperature the catalyst material in the element will cause combustion of methane which comes into contact with it in the presence of oxygen. Since the compensating element also operates at a high temperature it is made such that it will not readily oxidise hydrocarbons which may come into contact with it when it is heated; a suitable arrangement is for the resistor 7 to be in the form of a length of platinum wire shaped similarly to the wire 1 and having its coiled part embedded in a pellet of alumina whose size matches that of the pellet 6, the pellet of the compensating element being formed by decomposition of an aluminium compound and being subsequently boiled in potassium hydroxide solution to inhibit any possible catalytic activity.

With the bridge circuit energised to heat the gas-sensitive and compensating elements, an atmosphere to be tested is brought into contact with them in a similar manner for the two devices; systems using gas flow or diffusion to effect such contact are well known in the art and therefore need not be described here. The bridge circuit is initially calibrated with the two elements in contact with normal air, the bridge being balanced, as indicated by zero deflection of the meter 11, by adjustment of the resistor 8. Thus, when methane is present in the atmosphere under test, the increase in temperature of the gas-sensitive element caused by the combustion of methane at the catalyst material will result in an increase in the resistance of the wire 1, but no corresponding increase will occur for the resistor 7. The bridge will therefore go out of balance, the resulting deflection of the meter 11 giving an indication of the methane concentration. The use of the compensating element is of course desirable to take account of possible fluctuations in parameters such as the voltage of the source 10 and the temperature and flow rate of the atmosphere under test.

There follows a discussion of results which have been obtained with gas-sensitive elements as described with reference to FIG. 1, when operated in a circuit as described with reference to FIG. 2; in all cases the operating temperature of the element was approximately 550° C., corresponding to a power consumption in the element of about 420 milliwatts. For convenience the elements will be referred to as of Types I, II and III, in correspondence with which of the Examples described above was applicable in the formation of the pellet 6 of the element. By way of comparison, reference will also be made to results obtained with conventional pellistors of the known type referred to in the description of Example I, operated under subtantially the same conditions as for the elements according to the invention.

Figure 3:
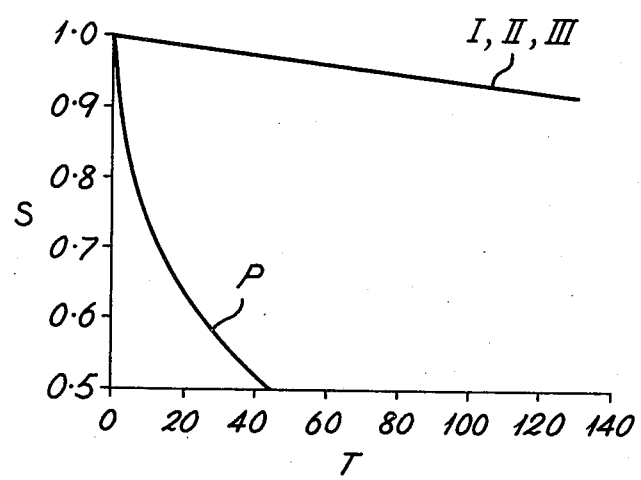
FIGS. 3 and 4 are diagrams illustrating the results obtainable by use of the invention.
Figure 4:
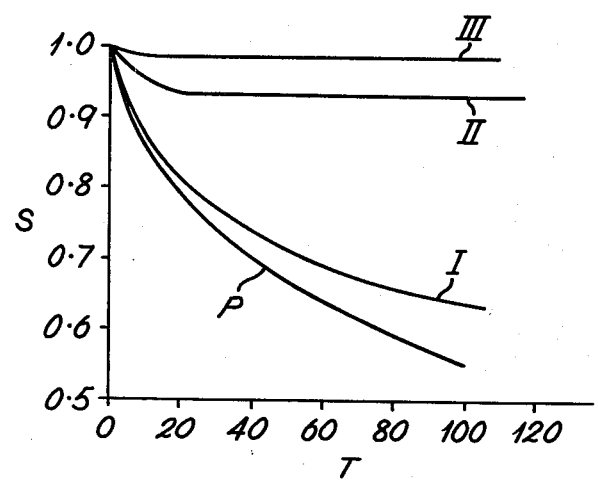

FIG. 3 illustrates results obtained when operating the elements continuously while exposed to air containing 1% methane and ten parts per million of hexamethyl disiloxane, with the elements initially being in a freshly made condition; FIG. 4 illustrates results obtained similarly, but using air containing 1% methane and 0.25% hydrogen sulphide. In both cases the relative sensitivity to methane (S), given by the ratio of the reading of the meter 11 at a given time to the initial reading of the meter 11, is plotted against time (T) expressed in minutes. In FIG. 3 the line labelled (I, II, III) indicates the average behaviour for elements of all three Types I, II and III, whose performance is very similar in this case, while in FIG. 4 the lines labelled I, II and III respectively indicate the average behaviour for elements of the correspondingly numbered Types; in both cases the line labelled P indicates the average behaviour for conventional pellistors. The changes in sensitivity illustrated in FIG. 3 are permanent, whereas those illustrated in FIG. 4 are largely reversible, i.e. hexamethyl disiloxane acts as a catalyst poison while hydrogen sulphide acts primarily as a catalyst inhibitor. As will be seen from FIG. 3, elements of all three Types exhibit much greater resistance than conventional pellistors to poisoning by hexamethyl disiloxane, their sensitivities to methane decreasing linearly at a rate which typically results in a loss of only about 10% sensitivity over a period of 150 minutes; in no case was there a loss of 10% sensitivity in a period of less than 100 minutes. In respect of resistance to inhibition and possible poisoning by hydrogen sulphide, however, the behaviour of the elements shows substantial differences, as will be seen from FIG. 4. In this respect, elements of Type I show only a modest improvement over conventional pellistors, whereas elements of Types II and III are very much superior; both exhibit negligible changes in sensitivity after an initial fairly rapid decrease (of about 7% for elements of Type II and less than 2% for elements of Type III).

It is thought that the results discussed above in respect of resistance to poisoning by hexamethyl disiloxane are primarily dependent on physical factors. Firstly, the dispersion of the catalyst metal throughout the pellet 6 in an element as described with reference to FIG. 1 is believed to result in a large increase in the effective surface area available for the combustion reaction as compared with the case of a conventional pellistor. Secondly, the size of the pores in the pellet 6 is believed to be sufficiently small to restrict access of hexamethyl disiloxane while allowing free access of methane and oxygen to the catalyst metal. It is expected that these considerations would be applicable also in respect of resistance to poisoning by other components of high molecular weight. The second of the factors just mentioned is not thought to be of any significance in relation to the results discussed above in respect of resistance to inhibition and possible poisoning by hydrogen sulphide. The differences between the three Types of element in this case are believed to be primarily dependent on chemical factors, and it could therefore be expected that similar differences would apply in respect of resistance to inhibition or poisoning by other sulphur compounds. It may be appropriate here to draw an analogy with the case of oxidation, since rhodium and platinum do not readily form oxides in air, whereas palladium does.

Tests similar to those for which the results are illustrated in FIGS. 3 and 4 have also been carried out using air containing 1% methane and 100 parts per million of trichloroethylene. After a period of 60 minutes, it was found that there had been a negligible change of sensitivity for elements of Type III, a 15% decrease of sensitivity for elements of Type II, and a 30% decrease of sensitivity for elements of Type I; this last figure is similar to that which is obtained for conventional pellistors.

From the foregoing results it can be seen that, considered solely from the point of view of resistance to poisoning and inhibition, elements of the three Types can be ranked in the order III, II, I. It should be emphasised, however, that those results are quoted in terms of relative sensitivites and that the absolute sensitivity for elements of Type III is much lower than that for elements of Types I and II. Typical figures for initial sensitivity with an operating temperature of 550° C. are 35 millivolts per 1% methane for elements of Type I, 30 millivolts per 1% methane for elements of Type II, and 18 millivolts per 1% methane for elements of Type III; for conventional pellistors operated at the same temperature the initial sensitivity normally lies in the range 30-34 millivolts per 1% methane, so that elements of Types I and II are closely comparable with conventional pellistors in this respect. To obtain a sensitivity comparable with that of a conventional pellistor operated at 550° C., it would be necessary to operate an element of Type III at a temperature of about 700° C., and this would in many cases entail a prohibitively high power consumption for use in a practical instrument. For many applications, therefore, it is likely that, having regard to all the relevant performance factors, elements of Type II would be preferable to those of Types I and III.

The long term stability of elements of Types I and II has been investigated by operating them in a circuit as described with reference to FIG. 2 while exposed continuously to normal air and intermittently tested by adding 1% methane to the air. The results were satisfactory, although not as good as for conventional pellistors. Thus the sensitivity of elements of Type I was found to decrease by about 10% over a period of three months, while the sensitivity of elements of Type II was found to decrease by about 3% over a period of one month; with conventional pellistors the fall in sensitivity would typically be about 10% in four years. The elements subjected to these investigations were found subsequently to exhibit substantially the same resistance as initially to poisoning by hexamethyl disiloxane.

It may also be noted that elements of all three Types exhibit similar response times for changes of methane concentration to those of conventional pellistors operated under the same conditions.

Tests similar to some of those discussed above have also been carried out using butane instead of methane as the combustible gas to be detected. The results obtained were generally similar to those for the tests discussed above.

Gas-sensitive elements as described with reference to FIG. 1 can of course also be used in arrangements (of a kind known per se) in which the temperature of the element is maintained substantially constant at an appropriate value by automatic variation of the current flowing through the wire 1, the magnitude of the necessary current providing an indication of the concentration of the combustible gas to be detected in an atmosphere brought into contact with the element; in such an arrangement it is convenient also to use the resistance of the wire 1 as the parameter to which the automatic control system for the current responds.

While it is convenient to use the form of element described with reference to FIG. 1 when it is required to provide more or less direct replacements for conventional pellistors in gas detection instruments, it will be apparent that the invention can also be utilised in other forms of gas-sensitive element of the kind specified. In particular it is envisaged that the invention would have useful application in cases where the electrical resistor of the element is in the form of a metallic coating on a ceramic substrate which serves to support the catalyst material.

It will also be appreciated that in performing the invention other compounds of metals of the platinum group can be utilised in place of those specifically mentioned in the Examples described above. As in the case of Example I, it would be preferred when the metal employed is palladium for the initial solution also to incorporate a thorium compound which is converted into thoria in the resultant catalyst material.

We claim:

1. A gas-sensitive element comprising:
a catalyst material exposed for contact with a sample of an atmosphere to be tested, said catalyst material being in the form of a coherent mass produced by heating a deposit made from an aqueous slurry of alumina containing in solution at least one compound of a metal of the platinum group, the particle size of the alumina in said slurry being no greater than 0.1 micron; and
an electrical resistor associated with said catalyst material and operable both as a heater for bringing said catalyst material to a temperature at which it can cause combustion of at least one gas to be detected and as a thermal sensor for detecting any thermal effect on said catalyst material caused by the occurrence thereon of a combustion reaction.

2. A gas-sensitive element according to claim 1, in which said coherent mass is in the form of a pellet within which is embedded a coiled part of a wire which constitutes said resistor.

3. A gas-sensitive element according to claim 2, in which said wire has an alumina coating.

4. A gas-sensitive element according to claim 1, in which said compound is a compound of palladium.

5. A gas-sensitive element according to claim 4, in which said compound is ammonium chloropalladite and said slurry also contains thorium nitrate in solution.

6. A gas-sensitive element according to claim 1, in which said compound is a compound of rhodium.

7. A gas-sensitive element according to claim 6, in which said compound is ammonium chlororhodite.

8. A gas-sensitive element according to claim 1, in which said compound is a compound of platinum.

9. A gas-sensitive element according to claim 8, in which said compound is chloroplatinic acid.

10. A gas-sensitive element according to claim 1 wherein the catalyst is prepared by making an aqueous solution of either (1) ammonium chloropalladite and thorium nitrate at respective concentrations of 0.45 and 1.18 moles per liter, (2) ammonium chlororhodite at a concentration of 0.23 moles per liter or (3) chloroplatinic acid at a concentration of 0.45 moles per liter, adding nitric acid to the aqueous solution in an amount to adjust the pH to a value between 0 and 1, producing a slurry by mixing this solution with gamma alumina having a particle size of 0.05 micron in the proportions of 0.36 gram of alumina to one ml of the solution, the alumina being predominantly in the form of sponge-like aggregates having dimensions in the range 1–5 microns and having a specific surface area in the range 100–120 meters$^2$/gram.

11. A gas sensitive element according to claim 10 wherein the catalyst is prepared by making the solution of ammonium chloropalladite and thorium nitrate at respective concentrations of 0.45 and 1.18 moles per liter.

12. In a process for preparing a gas-sensitive element comprising a catalyst material exposed for contact with a sample of an atmosphere to be tested, an electrical resistor associated with said catalyst material and operable both as a heater for bringing said catalyst material to a temperature at which it can cause combustion of at least one gas to be detected and as a thermal sensor for detecting any thermal effect on said catalyst material caused by the occurrence thereon of a combination reaction, the improvement comprising making an aqueous slurry of alumina containing in solution at least one compound of a metal of the platinum group, the particle size of the alumina in said slurry being no greater than 0.1 micron, depositing said slurry on said resistor, and heating said deposited slurry to produce a coherent mass of said catalyst material.

13. A process according to claim 12 in which said compound is a compound of palladium.

14. A process according to claim 13 in which said compound is ammonium chloropalladite and said slurry also contains thorium nitrate in solution.

15. A process according to claim 12 in which said compound is a compound of rhodium.

16. A process according to claim 15 in which said compound is ammonium chlororhodite.

17. A process according to claim 12 in which said compound is a compound of platinum.

18. A process according to claim 17 in which said compound is chloroplatinic acid.

19. A process according to claim 12 in which the slurry is deposited only on the resistor.

20. In a process for preparing a gas-sensitive element comprising a catalyst material exposed for contact with a sample of an atmosphere to be tested, an electrical resistor associated with said catalyst material and operable both as a heater for bringing said catalyst material to a temperature at which it can cause combustion of at least one gas to be detected and as a thermal sensor for detecting any thermal effect on said catalyst material caused by the occurrence thereon of a combustion reaction, the improvement comprising making an aqueous slurry of alumina containing in solution at least one compound of a metal of the platinum group, the particle size of the alumina in said slurry being no greater than 0.1 micron, making a deposit from said slurry and heating said deposit to produce a coherent mass of said catalyst material.

* * * * *